(12) United States Patent
Segel et al.

(10) Patent No.: US 8,233,989 B1
(45) Date of Patent: *Jul. 31, 2012

(54) SYSTEM AND METHOD FOR FITTING A HEARING PROSTHESIS SOUND PROCESSOR USING ALTERNATIVE SIGNALS

(75) Inventors: Philip A. Segel, Englewood, CO (US); Edward H. Overstreet, Valencia, CA (US); Tracey L. Kruger, Valencia, CA (US); Lakshmi N. Mishra, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/083,173

(22) Filed: Apr. 8, 2011

Related U.S. Application Data

(63) Continuation of application No. 12/250,512, filed on Oct. 13, 2008, now Pat. No. 7,933,657, which is a continuation of application No. 10/651,653, filed on Aug. 29, 2003, now Pat. No. 7,496,406.

(60) Provisional application No. 60/407,173, filed on Aug. 30, 2002.

(51) Int. Cl.
*A61N 1/04* (2006.01)
(52) U.S. Cl. ............... 607/57; 607/56; 607/58; 607/136
(58) Field of Classification Search ............ 607/55, 607/56, 57, 136
See application file for complete search history.

(56) References Cited

U.S. PATENT DOCUMENTS

| | | | |
|---|---|---|---|
| 3,751,605 A | 8/1973 | Michelson | |
| 3,766,331 A | 10/1973 | Zink | |
| 4,400,590 A | 8/1983 | Michelson | |
| 4,495,384 A | 1/1985 | Scott et al. | |
| 4,819,647 A | 4/1989 | Byers et al. | |
| 5,603,726 A | 2/1997 | Schulman et al. | |
| 5,626,629 A | 5/1997 | Faltys et al. | |
| 5,800,475 A * | 9/1998 | Jules | 607/57 |
| 5,938,691 A | 8/1999 | Schulman et al. | |
| 6,067,474 A | 5/2000 | Schulman et al. | |
| 6,078,838 A | 6/2000 | Rubinstein | |
| 6,129,753 A | 10/2000 | Kuzma | |

(Continued)

FOREIGN PATENT DOCUMENTS
WO 03/015863 A2 2/2003

OTHER PUBLICATIONS

Rubinstein et al., "The Neurophysiological Effects of Simulated Auditory Prosthesis Stimulation," Second Quarterly Progress Report No. 1-DC-6-2111, May 27, 1997, Iowa City, Iowa.

(Continued)

*Primary Examiner* — Niketa Patel
*Assistant Examiner* — Alyssa M Alter
(74) *Attorney, Agent, or Firm* — AdvantEdge Law Group, LLC

(57) ABSTRACT

Alternative stimuli, i.e., stimuli other than the constant amplitude stimuli used in prior fitting schemes, are used to set the parameters of a hearing prosthesis, such as a cochlear implant system. The use of such alternative stimuli allows the entire fitting process to be completed in a very short time period, and generally eliminates the need for secondary adjustments. In one preferred embodiment, the alternative stimuli comprise white noise that is internally generated within the speech processor.

16 Claims, 6 Drawing Sheets

U.S. PATENT DOCUMENTS

| | | | |
|---|---|---|---|
| 6,157,861 | A | 12/2000 | Faltys et al. |
| 6,195,585 | B1 | 2/2001 | Karunasiri et al. |
| 6,205,360 | B1 | 3/2001 | Carter et al. |
| 6,208,882 | B1 | 3/2001 | Lenarz et al. |
| 6,219,580 | B1 | 4/2001 | Faltys et al. |
| 6,249,704 | B1 | 6/2001 | Maltan et al. |
| 6,289,247 | B1 | 9/2001 | Faltys et al. |
| 6,295,467 | B1 | 9/2001 | Kollmeier et al. |
| 6,415,185 | B1 | 7/2002 | Maltan |
| 7,043,303 | B1 | 5/2006 | Overstreet |
| 7,076,308 | B1 | 7/2006 | Overstreet et al. |
| 7,107,101 | B1 | 9/2006 | Faltys |
| 7,117,038 | B1 | 10/2006 | Overstreet |
| 7,206,640 | B1 | 4/2007 | Overstreet |
| 7,496,406 | B1 | 2/2009 | Segel |
| 7,933,657 | B1 * | 4/2011 | Segel et al. .................... 607/57 |
| 2003/0195588 | A1 | 10/2003 | Fischell et al. |
| 2008/0221640 | A1 | 9/2008 | Overstreet et al. |

OTHER PUBLICATIONS

Van Wieringen et al., "Comparison of Procedures to Determine Electrical Stimulation Thresholds in Cochlear Implant Users," Ear and Hearing, vol. 22(6), 2001, pp. 528-538.

Zeng et al., "Loudness of Simple and Complex Stimuli in Electric Hearing," Annals of Otology, Rhinology & Laryngology, Supplement 166, Sep. 1995, vol. 104(9) Part 2, pp. 235-238.

\* cited by examiner

SYSTEM AND METHOD FOR FITTING A HEARING PROSTHESIS SOUND PROCESSOR USING ALTERNATIVE SIGNALS

This application is a Continuation of U.S. patent application Ser. No. 12/250,512, filed Oct. 13, 2008, which is a Continuation of Ser. No. 10/651,653, filed Aug. 29, 2003, which claims the benefit of U.S. Provisional Application Ser. No. 60/407,173, filed Aug. 30, 2002, which applications are incorporated herein by reference.

BACKGROUND OF THE INVENTION

The present invention relates to hearing prostheses, and more particularly to an improved technique for programming, or fitting, a cochlear implant system to a particular patient.

Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating form the respective sites. The patterns of electrical stimulation are derived from acoustic signals picked up by a microphone and transformed by a so-called speech processor that is programmed to meet the particular requirements of each patient. Several different schemes for processing the acoustic signal and transforming it into electrical stimuli have been developed and are well-described in the scientific literature and various patents. For purposes of the present invention, these schemes—also known as speech processing strategies—can generally be considered as either sequentially, partially-simultaneously or fully-simultaneously speech processing strategies.

The conventional setting of electrical stimulation levels in sound processors for cochlea implant systems—a process generally referred to as "fitting" the speech processor to a patient—has involved the stimulation of single channels (comprised of monopolar or bipolar stimulation pathways) employing stimuli that do not resemble the stimulation patterns inherent in the on-going speech signal. See, e.g., U.S. Pat. No. 5,626,629, incorporated herein by reference. Typically, during such fitting process, gated-bursts of some fixed burst duration and constant amplitude are delivered to the patient. This procedure of obtaining psychophysical measurements is often quite laborious. The patient's task is to set a level where sound is barely audible, and then set a level where sound is comfortably loud.

Disadvantageously, after going through the time-consuming and laborious cochlear-implant-fitting process, when the patient's microphone is enabled and speech stimuli are delivered to all channels, either sequentially, partially-simultaneously or fully-simultaneously, the psychophysically set levels bear little resemblance to the final parameters set in the patient's sound processor. Adjustments to the overall level of stimulation as well as other parameters tend to be required to mold the psychophysically derived parameters into a viable program that appropriately maps the perceived speech stimuli to electrical stimuli that may be delivered directly to the patient's cochlea. Hence, essentially two fitting procedures are typically required—one to set the psychophysical levels, and a second to make adjustments to such levels.

A further complication in setting levels in a sound processor is the fact that in cochlear-implant systems, which employ narrow pulse widths (e.g., 10.7 microseconds) and high rates of stimulation, obtaining single-channel measurements for estimates of comfortable loudness is not practical. At high rates of stimulation, the behavior of the electrically stimulated auditory system can mimic that of the normally healthy ear in that perception of constant amplitude stimuli cannot be maintained over time by all patients. Thus, the need arises, in setting the levels in cochlear implant processors, for using either actual speech stimuli, or stimuli that mimic the nature of speech.

SUMMARY OF THE INVENTION

The present invention addresses the above and other needs by using alternative stimuli, i.e., stimuli other than the constant amplitude stimuli used in prior fitting schemes, to set the parameters of a cochlear implant system. The use of such alternative stimuli advantageously allows the entire fitting process to be completed in a very short time period, and generally eliminates the need for secondary adjustments.

In accordance with one aspect of the present invention, modulated pulse trains with selectable degrees of amplitude modulation are delivered during the fitting process. These novel stimuli are delivered to the cochlear processor either in rapid sequential fashion, partially simultaneous fashion, or full simultaneous fashion to groups of channels within the speech processor. In this context, a "group" of channels may contain n channels, where n is an integer that may be as few as one channel or as large as the number of channels within the speech processor of the cochlear implant system. Advantageously, such modulated pulse trains mimic the time varying nature of speech stimuli sufficiently so as to allow the setting of the sound processor parameters in a single step without further adjustments.

In accordance with another aspect of the invention, various speech-like stimuli may be inputted during the fitting process in order to set the parameters of the sound processor. Such speech-like stimuli include, but are not necessarily limited to: (1) shaped bands of noise whose overall bandwidth is adjustable; (2) modulated bands of noise whose center frequencies are adjustable; (3) complex tonal stimuli whose spectra and various amplitude components are adjustable; or (4) speech tokens whose spectra and amplitude envelopes are well described.

In accordance with an additional aspect of the invention, modulated stimuli, in some embodiments, may be delivered directly through the band-pass filters of the sound processor via the fitting system rather than through an auxiliary port. The perceived loudness of such stimuli may then be adjusted as needed, e.g., according to prior known psychophysical procedures.

In accordance with yet another feature of the invention, in one embodiment, the modulated stimuli comprise white noise that is generated internal to the speech processor. Such white noise is then applied directly through the band-pass filters of the sound processor and processed through a multiplicity of channels in parallel so that stimuli resulting from the white noise are delivered to a selected group of electrodes, where the perceived loudness of the stimuli are adjusted as needed to a desired threshold level.

Advantageously, in some embodiments of the invention, the stimuli used by the invention during the sound processor setting procedure may be generated through a software module that may be incorporated into the cochlear implant processor fitting system, e.g., the CLARION® CII Bionic Ear® System, or the HiRes90K® System, available commercially from Advanced Bionics Corporation, of Sylmar, Calif., or other commercially-available cochlear implant systems.

In operation, at least some embodiments of the invention may adjust the level of the delivered stimuli according to known perceptual loudness contours derived from normal hearing individuals (minimal audible field) or from known acoustic phenomena, such as the long-term spectrum of speech. Thus, e.g., stimuli may be delivered at the electrical equivalent of the long-term spectrum of speech, at a level representing the detection abilities of normal hearing individuals, or at any point in between.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
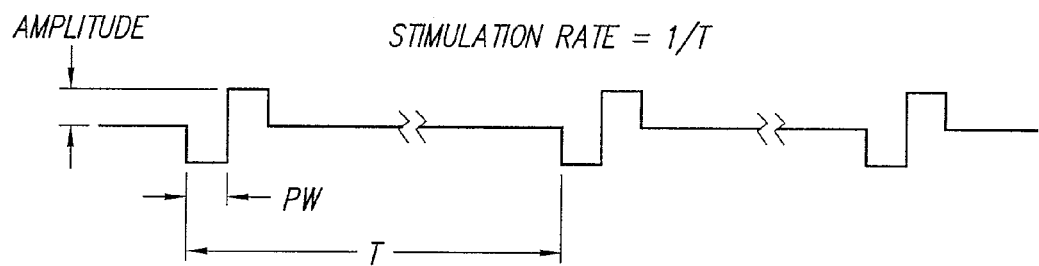
FIG. 1 is a current stimulation waveform that defines the stimulation rate (1/T) and biphasic pulse width (PW) associated with electrical stimuli, as those terms are used in the present application.

FIG. 1 shows a waveform diagram of a biphasic pulse train, and defines stimulation rate, pulse width and pulse amplitude.

Figure 2A:
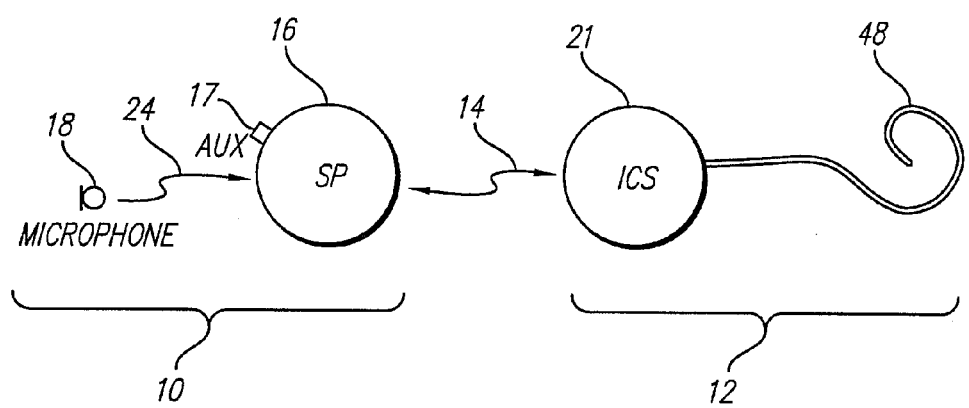
FIGS. 2A and 2B respectively show a cochlear implant system and a partial functional block diagram of the cochlear stimulation system, which system is capable of providing high rate pulsatile electrical stimuli.

FIG. 2A shows a cochlear stimulation system that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. An auxiliary input port 17 may also be part of the speech processor 16 to allow input signals from a source other than the microphone 18 to be input into the SP 16.

The cochlear stimulation portion 12 includes an implantable cochlear stimulator (ICS) 21 and an electrode array 48. The electrode array 48 is adapted to be inserted within the cochlea of a patient. The array 48 includes a multiplicity of electrodes, e.g., sixteen electrodes, spaced along its length, that are selectively connected to the ICS 21. The electrode array 48 may be substantially as shown and described in U.S. Pat. No. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16, auxiliary input port 17 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP 16 to the ICS 21. In some embodiments, data and status signals may also be sent from the ICS 21 to the SP 16.

In recent cochlear implant systems, as shown more particularly below in FIG. 2B, at least certain portions of the SP 16 are included within the implantable portion of the overall cochlear implant system, while other portions of the SP 16 remain in the external portion of the system. In general, at least the microphone 18 (and auxiliary input port 17, if used) and associated analog front end (AFE) circuitry 22 will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. Alternatively, electrical signals may be input directly into the auxiliary input port 17 from a suitable signal source. The SP 16 processes the converted acoustic signals received from the microphone, or the electrical signals received through the auxiliary input port 17, in accordance with a selected speech processing strategy in order to generate appropriate control signals for controlling the ICS 21. In operation, such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike early cochlear implant systems, more modern cochlear implant systems advantageously confine such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. In accordance with the present invention, an auto-conditioning with high resolution (ACHR) strategy is used which stimulates the implanted electrodes with a high rate pulsatile pattern that is amplitude modulated by the sound information. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one wherein stimulation currents, either analog or pulsatile, are applied to the electrodes of two or more channels, but not necessarily all of the channels, at the same time. Examples of each type are given in U.S. Pat. No. 6,289,247, incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsatile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to apply a high rate biphasic stimulation pulse train to each of the pairs of electrodes of selected channels in accordance with a selected strategy, and modulate the pulse amplitude of the pulse train as a function of information contained within the sensed acoustic signal, or the received auxiliary input signal.

Figure 2B:
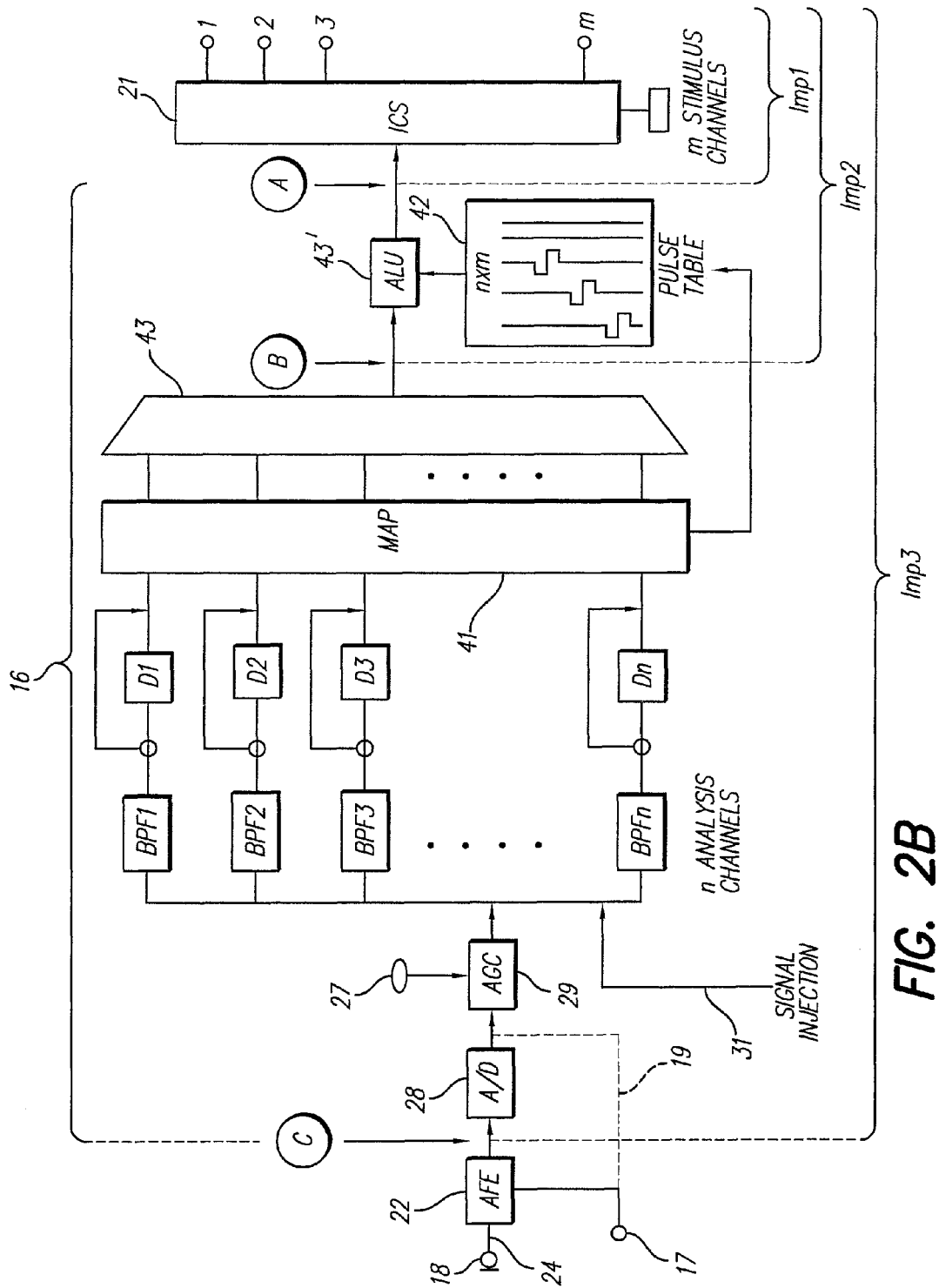

Turning next to FIG. 2B, a partial block diagram of a representative cochlear implant is shown. More particularly, FIG. 2B shows a partial functional block diagram of the SP 16 and the ICS 21 of an exemplary cochlear implant system capable of providing a high rate pulsatile stimulation pattern. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal.

A complete description of the functional block diagram of the cochlear implant system shown in FIG. 2B is generally found in U.S. Pat. No. 6,219,580, incorporated herein by reference. It is to be emphasized that the functionality shown in FIG. 2B is only representative of one type of exemplary cochlear implant system, and is not intended to be limiting. The details associated with a given cochlear implant system are not critical to understanding and practicing the present invention.

One important addition to the functional block diagram of the cochlear implant system illustrated in FIG. 2B that may be used by the present invention, which is not shown or described in the U.S. Pat. No. 6,219,580, is the use of an internal signal injection port 31. Such port 31 allows appropriate internal signals, generated within the speech processor circuits, to be injected into the signal processing path immediately after the AGC circuit 29. This port differs from the external auxiliary port 17 in that it is not intended for use by external signals, and the internal signals applied to it are not processed by the AFE circuits 22, the A/D circuits 28, or the AGC circuits 29, as are signals received through the auxiliary input port 17 or the microphone 18. Thus, for example, an appropriate internally-generated signal may be generated by appropriate circuits included within the speech processor circuits 16 and applied to the internal signal injection port 31, and thereafter be processed by the speech processor circuits and other circuits (e.g., pulse generator circuits) within the cochlear implant system in order to facilitate fitting of the cochlear implant system to a particular patient or user. As will be described in more detail below in conjunction with the description of FIG. 6, one preferred embodiment of the invention applies white noise, generated by circuits within the speech processor, to the internal injection port 31, and then processes such noise through selected bands or groups of channels simultaneously, resulting in noise stimuli being applied to multiple electrodes simultaneously. Being able to sense noise stimuli on multiple electrodes in this fashion allows the "M" levels of the patient to be quickly identified and set during a fitting session.

In the manner described in the U.S. Pat. No. 6,219,580, the cochlear implant functionally shown in FIG. 2B provides n analysis channels that may be mapped to one or more stimulus channels. That is, as seen in FIG. 2B, after the incoming sound signal is received through the microphone 18 or auxiliary input port 17, and the analog front end circuitry (AFE) 22, it is digitized in an analog to digital (A/D) converter 28, and then subjected to appropriate gain control (which may include compression) in an automatic gain control (AGC) unit 29. (It should be noted that in some instances the signal input into the auxiliary input port 17 may already be digitized, in which case a signal path 19 is provided that bypasses the A/D converter 28.) After appropriate gain control, the signal is divided into n analysis channels, each of which includes a bandpass filter, BPFn, centered at a selected frequency. The signal present in each analysis channel is processed as described more fully in the U.S. Pat. No. 6,219,580, and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through this multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern cochlear implant system, such as the CII Bionic Ear® system, or the HiRes90K® system, manufactured by Advanced Bionics Corporation of Sylmar, Calif., advantageously puts at least a portion of the speech processor 16 within the implanted portion of the system. For example, a cochlear implant system may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

Future generations of cochlear implant systems may incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), need only have rate commensurate with the input signal received through the microphone 18 or the auxiliary input port 17.

With the preceding as background information relative to a typical cochlear implant system, the present invention provides a streamlined way of "fitting" such a cochlear implant system to a given patient. More particularly, the present invention uses alternative stimuli, i.e., stimuli other than the constant amplitude stimuli used in prior fitting schemes to determine "T" and "M" levels, see, e.g., U.S. Pat. Nos. 5,626,629 and 6,289,247, incorporated herein by reference, to set the parameters of a cochlear implant system. The use of such alternative stimuli by the present invention advantageously allows the entire fitting process to be completed in a very short time period, and generally eliminates the need for secondary adjustments.

Figure 3:
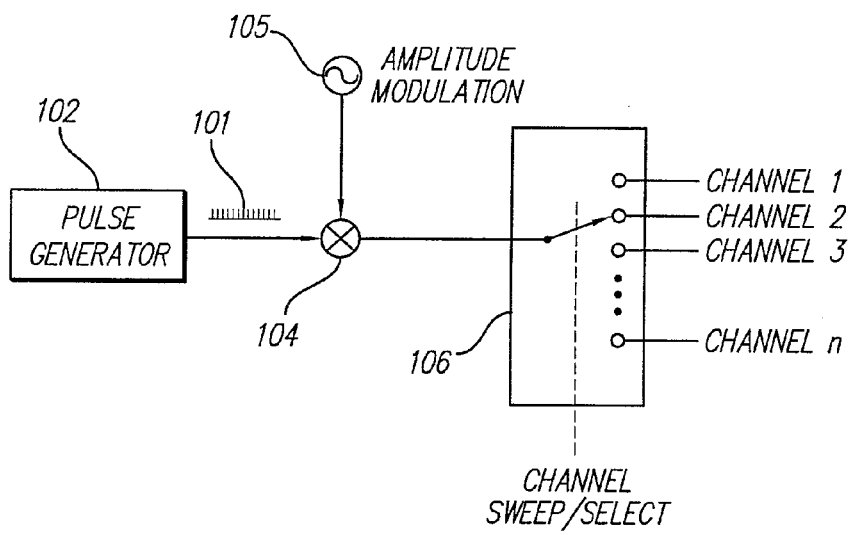
FIG. 3 illustrates application of speech-like stimuli, e.g., an amplitude modulated high rate pulsatile waveform, during the fitting process of a cochlear implant system in accordance with the invention.

For example, as shown in FIG. 3, one embodiment of the present invention generates modulated pulse trains with selectable degrees of amplitude modulation. Such amplitude modulated pulse trains are delivered to the speech processor during the fitting process either in rapid sequential fashion, partially simultaneous fashion, or full simultaneous fashion to groups of channels within the speech processor. In this context, a "group" of channels may contain n channels, where n is an integer that may be as few as one channel or as large as the number of channels within the speech processor of the cochlear implant system. Advantageously, such modulated pulse trains mimic the time varying nature of speech stimuli sufficiently so as to generally allow the setting of the sound processor parameters in a single step without further adjustments on a channel-by-channel basis. Such modulated pulse trains mimic the time varying nature of speech stimuli sufficiently so as to allow the setting of the sound processor parameters in a single step without further adjustments.

Thus, as seen in FIG. 3, a pulse generator 102 generates a stream of pulses 101. The frequency of such stream of pulses 101 is preferably greater than about 2 KHz. e.g., with a period T less than about 500 microseconds (μsec). The pulse width, PW, is relatively narrow, e.g., from about 11 μsec (e.g., 10.8 μsec) to about 75 μsec, but preferably around 21 μsec. Such pulses 101 are then amplitude modulated in a modulator 104 with a selected modulation signal 105, e.g., a signal that provides speech-like stimuli, to produce an amplitude modulated stream of pulses 103. The amplitude modulated stream of pulses 103 is then applied, e.g., on a channel-by-channel basis through an appropriate multiplexer 106, or equivalent, or to groups of channels, to the inputs of the respective channels. Appropriate parameters associated with each channel are then adjusted, as the amplitude modulated pulsatile signal 103 is applied to the channel, or to the channel group, to set the operating parameters of the speech processor. After the fitting session is complete, and the needed operating parameters of the speech processor have been set, the patient, or user of the cochlear implant system, is able to better perceive sound signals received through the microphone 18, or auxiliary input port 17, as the appropriate sound.

The modulation signal 105 may take many forms. In one embodiment, for example, the modulation signal mimics various speech-like stimuli. Such speech-like stimuli may include, for example, the following stimuli:

1. Shaped bands of noise whose overall bandwidth is adjustable. These bands may be externally inputted into the auxiliary input port 17 of the cochlear speech processor 16, or the internal input port 31, at levels following the long-term spectrum of speech in each band. For example, shaped bands of noise may be used that cover the input center frequencies of 1, 3, 5 or more channels.
2. Modulated bands of noise whose center frequencies are adjustable.
3. Complex tonal stimuli whose spectra and various amplitude components are adjustable.
4. Speech tokens whose spectra and amplitude envelopes are well described.

Figure 4A:
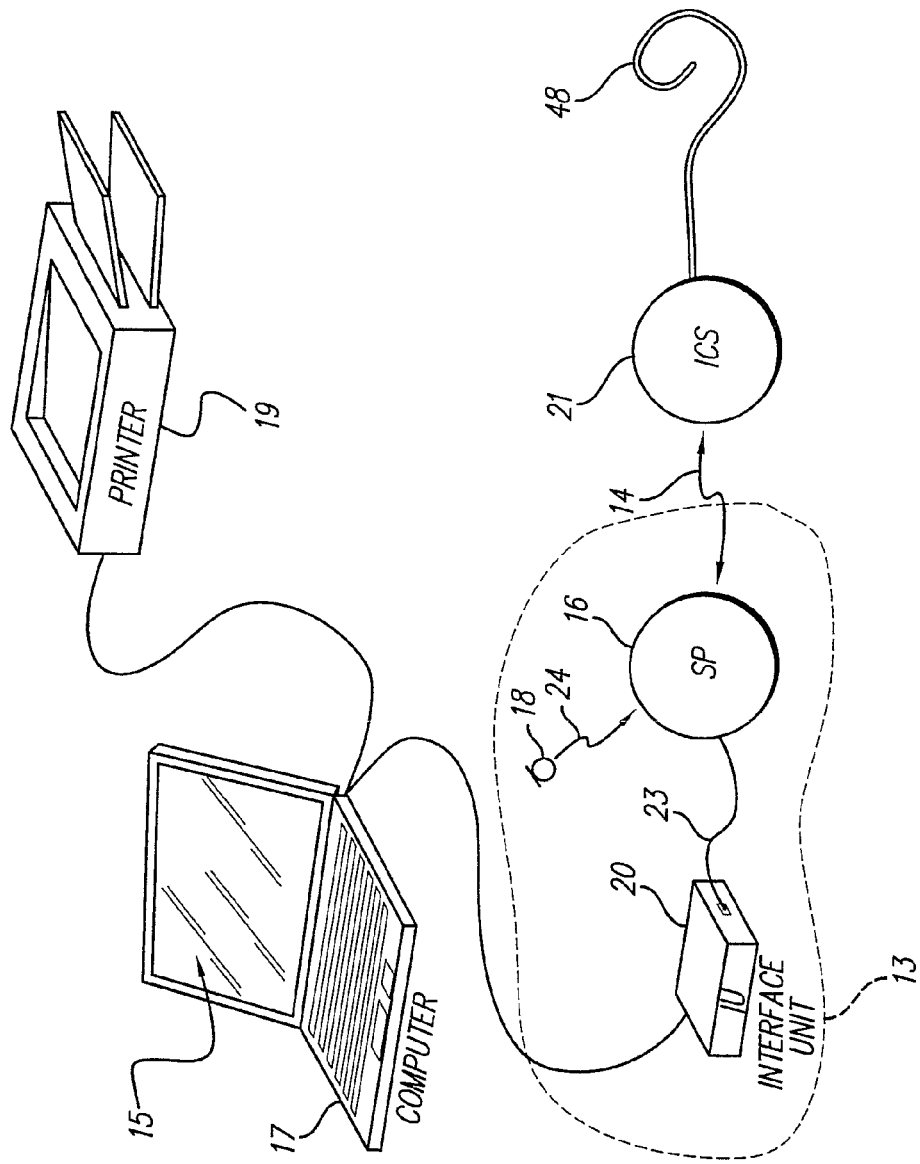
FIGS. 4A and 4B show respective fitting configurations that may be used during a fitting session.
Figure 4B:
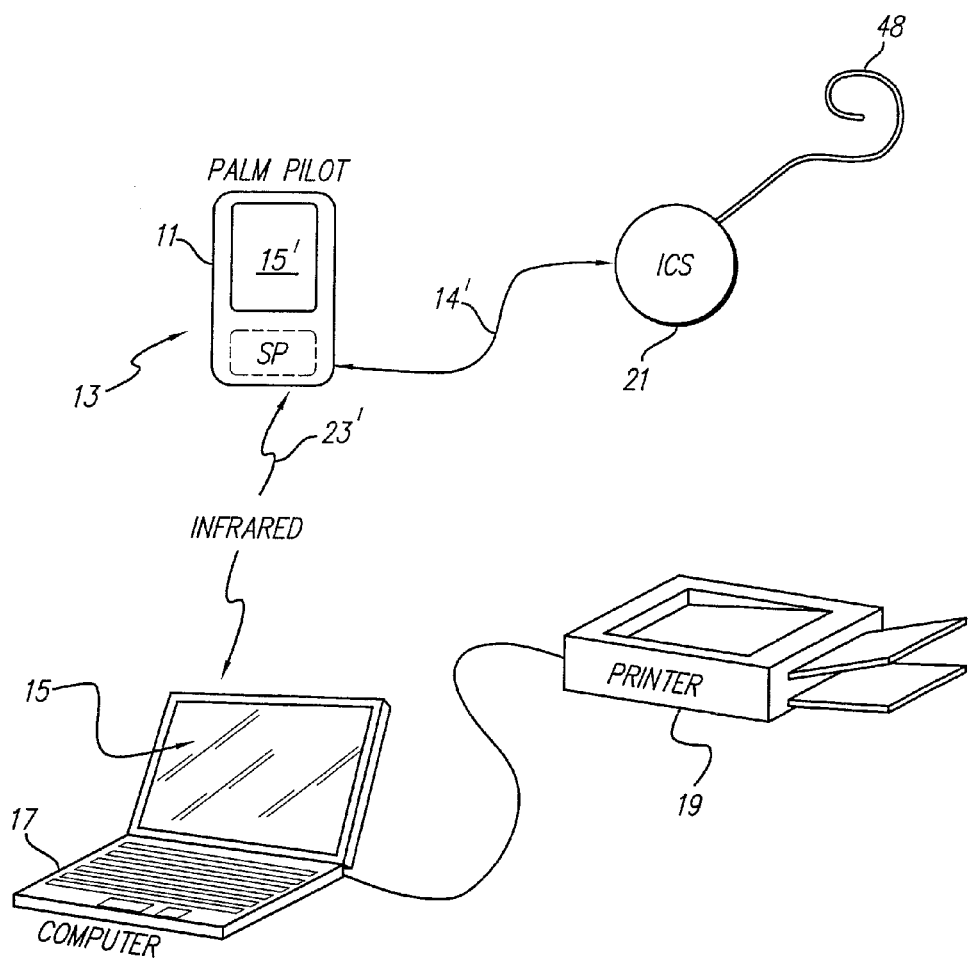

Representative fitting system configurations that may be used with the invention are illustrated in FIGS. 4A and 4B. The alternative stimuli provided by the present invention in order to simplify the fitting process may be used with either of these fitting configurations, or other configurations.

As seen in FIG. 4A, there is shown a block diagram of the basic components used to fit a given patient with a cochlear implant system. As seen in FIG. 4A, the implant system is as shown in FIG. 1, and includes the SP 16 linked to an ICS 21, and the ICS is connected to an electrode array 48. A microphone 18 is also linked to the SP 16 through a suitable communication link 24. A laptop computer 170, or other type of computer, or equivalent device, is coupled to the speech processor 16 through an interface unit (IU) 20, or equivalent device. The type of linkage 23 established between the IU 20 and the SP 16 will vary depending upon whether the SP 16 is implanted or not. Any suitable communications link 23 may be used, as is known in the art, and thus the details of the link 23 are not important for purposes of the present invention. It should be noted that for some applications, the IU 20 may be included within the computer 170 (e.g., as a communications interface already present within the computer, e.g., a serial port, or other built-in port, e.g., an IR port).

The computer 170, with or without the IU 20, provides input signals to the SP 16 that simulate acoustical signals sensed by the microphone 18, or received through the auxiliary input port 17, and/or provide command signals to the SP 16. In some instances, e.g., when testing the patient's threshold levels, the signals generated by the computer 170 replace the signals normally sensed through the microphone 18. In other instances, e.g., when testing the patient's ability to comprehend speech, the signals generated by the computer 170 provide command signals that supplement the signals sensed through the microphone 18.

The laptop computer 170 (or equivalent device) provides a display screen 15 on which selection screens, stimulation templates and other information may be displayed and defined. Such computer 170 thus provides a very simple way for the audiologist or other medical personnel, or even the patient, to easily select and/or specify a particular pattern of stimulation parameters that may be thereafter used, even if for just a short testing period, regardless of whether such stimulation pattern is simple or complex. Also shown in FIG. 4A is a printer 19 which may be connected to the computer 170, if desired, in order to allow a record of the selection criteria, stimulation templates and pattern(s) that have been selected and/or specified to be printed.

FIG. 4B illustrates an alternative fitting system that may also be used. In FIG. 4B, the ICS 21 is linked to a speech processor configured or emulated within a palm personal computer (PPC) 11, such as a Palm Pilot, or equivalent processor, commercially available, e.g., from Hewlett Packard. Such PPC 11 includes its own display screen 15' on which some graphical and textual information may be displayed. In use, the PPC 11 is linked, e.g., through an infrared link 23', to another computer, 170, as necessary. Typically, the functions of the SP and related devices are stored in a flashcard (a removable memory card that may be loaded into the PPC 11), thereby enabling the PPC 11 to perform the same functions of those elements encircled by the dotted line 13 in FIG. 4A. The PPC 11 is coupled to the ICS 21 through a suitable data/power communications link 14'.

Figure 5:
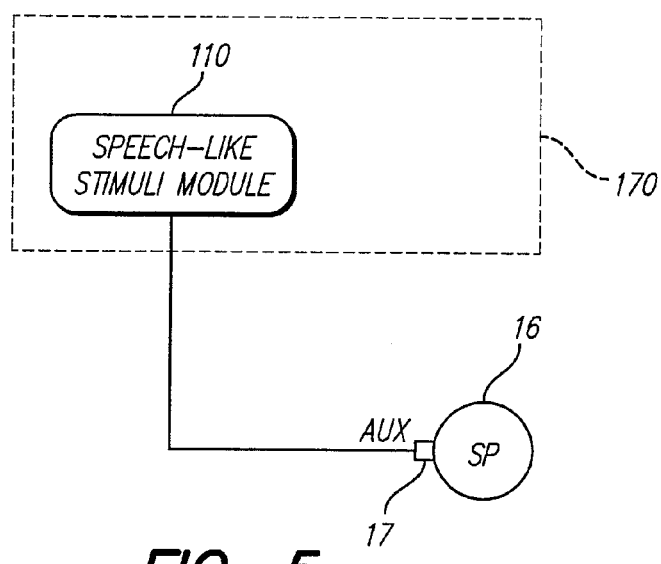
FIG. 5 illustrates a preferred configuration for applying speech-like stimuli to the speech processor of a cochlear implant system during a fitting session.

Advantageously, all of the stimuli used by the present invention during the sound processor setting procedure (or fitting process) may be generated through a software module 110 that is incorporated into the computer 170, or equivalent processor, as illustrated generally in FIG. 5. Moreover, as additionally illustrated in FIG. 5, and as a further simplification to the fitting process, the software module 110 may be linked directly to the auxiliary input port 17 of the speech processor 16, thereby eliminating the need for an interface unit 20, or equivalent device (see FIG. 4A).

As a further variation of the invention, the software module, or equivalent processor, used to generate the stimuli used by the invention may be acoustically linked with the microphone 18 used by the speech processor 16 (see FIG. 4A). That is, the modulated stimuli used by the invention may, in some embodiments, be inputted into the speech processor via the microphone link rather than through an interface unit or through the auxiliary port.

In operation, the level of the stimuli provided by the invention during the fitting process are adjusted according to known perceptual loudness contours derived from normal hearing individuals (minimal audible field) or from known acoustic phenomena, such as the long-term spectrum of speech. Thus, stimuli may be delivered at the electrical equivalent of the long-term spectrum of speech, at a level representing the detection abilities of normal hearing individuals, or at any point in between.

Figure 6:
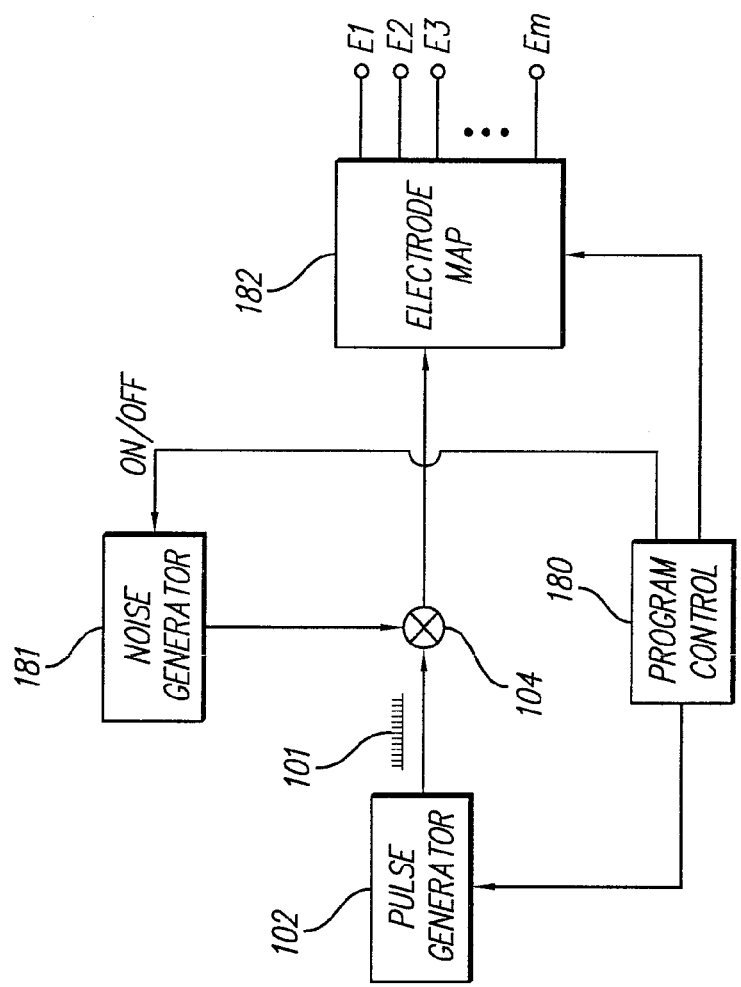
FIG. 6 illustrates a preferred configuration for applying noise stimuli to selected multiple channels of the cochlear implant system during a fitting session.

Next, with reference to FIG. 6, a preferred manner of implementing a fitting session in accordance with the invention is illustrated. As seen in FIG. 6, a pulse generator 102 generates a stream of pulses 101. The frequency of such stream of pulses 101 is preferably greater than about 2 KHz. e.g., with a period T less than about 500 microseconds (μsec). The pulse width, PW, is relatively narrow, e.g., from about 5 μsec to about 75 μsec, but preferably around 11 μsec (e.g., 10.8 μsec). Such pulses 101 are then modulated in a modulator 104 with a noise signal generated by a noise generator 181. Preferably, the noise generator 181 comprises a simple white noise generator realized using circuits already present within the implantable speech processor. The noise generator 181 is controlled during a fitting session, e.g., turned ON or OFF, by program control circuitry 180. The pulse generator 102 is likewise controlled by the control circuitry 180.

The output signal from the modulator 104 comprises a pulse train of white noise. This signal—a pulse train of white noise—is then processed simultaneously through a multiplicity of channels within the speech processor, resulting in stimuli being applied to a first group, or band, of electrodes through electrode map circuitry 182. The electrode map circuitry 182 applies the signal at its input to a selected group of electrodes, E1, E2, E3, ... Em, at its output. This mapping is, during a fitting session, controlled by the program control circuitry 180. Advantageously, applicants have discovered that by applying the noise stimuli to multiple electrodes simultaneously, a better, more true-to-life, representation of how the patient will perceive actual sound, is obtained. Thus, during a fitting session, the "M" levels (the stimulation current amplitude that results in comfortable perceived stimulation for each channel) for the group or band of channels where the noise stimuli are applied may be quickly determined and set.

By way of example, a typical fitting session using this embodiment of the invention may proceed as follows: (1) internally-generated white noise is generated and applied to the internal signal injection port; (2) the white noise is thereafter processed through a selected a first group or band of channels, e.g., so as to cause stimuli to be generated and applied to the patient through a first group or band of electrodes, e.g., electrodes E1, E2, E3 and E4; (3) the "M" levels (magnitude of the applied stimuli) for the first group of channels are adjusted to a comfortable level as perceived by the patient or user; and (4) the process is repeated for a second group of channels, a third group of channels, and so on, until stimuli have been applied through all the electrodes and all "M" levels have been set.

Electrode or channel groups (bands) used during this process may include overlapping channels or electrodes, i.e., an individual channel or electrode may be present in more than one group or band. For example, a first group of channels/electrodes may include electrodes E1, E2, E3, and E4; and a second group of channels/electrodes may include electrodes E3, E4, E5 and E6, a third group of channels/electrodes may include electrodes E5, E6, E7 and E8, and so on, with an overlap of two electrodes in each group or band. When such overlap exists, the "M" level of a particular channel may comprise an average of the "M" levels determined from each group.

In one preferred rapid fitting session of a cochlear implant system having sixteen channels and sixteen electrodes, there is no overlap of electrodes. Rather, white noise stimuli are first applied through a first electrode group comprising electrodes E1, E2, E3 and E4 and the "M" level for each corresponding channel is determined jointly with the other channels/electrodes in the group based on what feels comfortable to the patient (user). Next, white noise stimuli are applied through a second electrode group comprising electrodes E5, E6, E7 and E8, and the "M" level for each corresponding channel is again jointly determined based on patient perception. Next, white noise stimuli are applied through a third electrode group comprising electrodes E9, E10, E11 and E12, and the "M" level for each corresponding channel is again jointly determined based on patient perception. Finally, white noise stimuli are applied through a fourth electrode group comprising electrodes E13, E14, E15 and E16, and the "M" level for each corresponding channel is again jointly determined based on patient perception. Thus, in essentially four steps, each of which can normally be performed and completed in just a matter of minutes, or even seconds, appropriate "M" levels (for subsequent use by the cochlear stimulation system when sensing real sound through the microphone 18 and/or auxiliary port 17) may be set for all sixteen channels, thereby completing the fitting process.

While the invention herein disclosed has been described by means of specific embodiments and applications thereof, numerous modifications and variations could be made thereto by those skilled in the art without departing from the scope of the invention set forth in the claims.

What is claimed is:

1. A method of adjusting parameter settings of a hearing prosthesis associated with a particular patient comprising:
    generating modulated pulse trains that have selectable degrees of modulation, do not have a constant amplitude or frequency, and are configured to mimic the time varying nature of speech stimuli;
    delivering the modulated pulse trains to a sound processor of the hearing prosthesis during a "fitting" session; and
    using the modulated pulse trains to set the parameter settings of the hearing prosthesis during the "fitting" session without first determining a threshold level.

2. The method of claim 1 wherein the using of the modulated pulse trains to set the parameter settings of the hearing prosthesis is performed in a single step that requires no further adjustment to the parameter settings.

3. The method of claim 1 further including delivering the modulated pulse trains to the sound processor of the hearing prosthesis through a microphone coupled to the hearing prosthesis.

4. The method of claim 1 further including delivering the modulated pulse trains to the sound processor of the hearing prosthesis through an auxiliary input of the hearing prosthesis.

5. The method of claim 1 wherein the step of generating the modulated pulse trains comprises generating speech-like stimuli selected from the group consisting of:
    a. shaped bands of noise whose overall bandwidth is adjustable, wherein said bands of noise are externally inputted to the sound processor at levels following a long-term spectrum of speech in each band;
    b. modulated bands of noise whose center frequencies are adjustable;
    c. complex tonal stimuli whose spectra and various amplitude components are adjustable; and
    d. speech tokens.

6. The method of claim 5 wherein the hearing prosthesis comprises a multi-channel hearing prosthesis hearing prosthesis having a multiplicity of channels, and wherein the shaped bands of noise are selected to cover input center frequencies of 1, 3, 5 or more of said multiplicity of channels.

7. The method of claim 5 wherein the speech-like stimuli generated for use during the sound processor setting procedure are generated with the aid of a software module incorporated into the hearing prosthesis.

8. The method of claim 1 wherein the generating of the modulated pulse trains comprises modulating pulse trains according to perceptual loudness contours derived from normal hearing individuals.

9. The method of claim 1 wherein the generating of the modulated pulse trains comprises generating a pulse train and adjusting the level of the pulse train based on known acoustic phenomena.

10. The method of claim 9 wherein the known acoustic phenomena comprise a long-term spectrum of speech, and wherein the method further comprises using the modulated pulse trains to represent an electrical equivalent of the long-term spectrum of speech.

11. The method of claim 9 wherein the known acoustic phenomena comprise a long-term spectrum of speech, and wherein the method further comprises using the modulated pulse trains to represent the detection abilities of normal hearing individuals.

12. The method of claim 9 wherein the known acoustic phenomena comprise a long-term spectrum of speech, and wherein the method further comprises using the modulated pulse trains to represent any point between an electrical equivalent of the long-term spectrum of speech and detection abilities of normal hearing individuals.

13. The method of claim 1 further including delivering the modulated pulse trains to the sound processor of the hearing prosthesis by way of an interface unit connected to the hearing prosthesis.

14. A system comprising:
   means for generating modulated pulse trains that have selectable degrees of modulation, do not have a constant amplitude or frequency, and are configured to mimic the time varying nature of speech stimuli;
   means for delivering the modulated pulse trains to a sound processor of a hearing prosthesis during a "fitting" session; and
   means for using the modulated pulse trains to set the parameter settings of the hearing prosthesis during the "fitting session" without first determining a threshold level.

15. The system of claim 14 wherein the means for using the modulated pulse trains to set the parameter settings of the hearing prosthesis is configured to set the parameter settings in a single step that requires no further adjustment.

16. The system of claim 14 wherein the means for generating the modulated pulse trains comprises means for generating speech-like stimuli selected from the group consisting of:
   a. shaped bands of noise whose overall bandwidth is adjustable, wherein said bands of noise are externally inputted to the sound processor at levels following a long-term spectrum of speech in each band;
   b. modulated bands of noise whose center frequencies are adjustable;
   c. complex tonal stimuli whose spectra and various amplitude components are adjustable; and
   d. speech tokens.

* * * * *